United States Patent
Ito et al.

(10) Patent No.: US 7,090,780 B2
(45) Date of Patent: Aug. 15, 2006

(54) BACTERICIDE FOR USE IN WATER TREATMENT, METHOD FOR WATER TREATMENT AND APPARATUS FOR WATER TREATMENT

(75) Inventors: Akihiko Ito, Otsu (JP); Katsufumi Oto, Otsu (JP); Kazuya Sugita, Otsu (JP); Yoshinari Fusaoka, Otsu (JP)

(73) Assignee: Toray Industries, Inc., (JP)

( * ) Notice: Subject to any disclaimer, the term of this patent is extended or adjusted under 35 U.S.C. 154(b) by 312 days.

(21) Appl. No.: 10/432,583

(22) PCT Filed: Apr. 2, 2002

(86) PCT No.: PCT/JP02/03296

§ 371 (c)(1),
(2), (4) Date: May 23, 2003

(87) PCT Pub. No.: WO02/080671

PCT Pub. Date: Oct. 17, 2002

(65) Prior Publication Data

US 2004/0050800 A1 Mar. 18, 2004

(30) Foreign Application Priority Data

Apr. 5, 2001 (JP) .............................. 2001-106969
Aug. 6, 2001 (JP) .............................. 2001-237656

(51) Int. Cl.
*C02F 1/68* (2006.01)

(52) U.S. Cl. ...................... 210/764; 210/755; 210/169; 210/749; 210/753; 510/247; 510/253; 510/255; 422/17

(58) Field of Classification Search ................ 210/169, 210/749, 753, 755, 764; 510/247, 253, 255; 422/17

See application file for complete search history.

(56) References Cited

U.S. PATENT DOCUMENTS 5,057,229 A 10/1991 Schulenburg (Continued)

FOREIGN PATENT DOCUMENTS

CN 1096010 A 12/1994

(Continued)

OTHER PUBLICATIONS

ALCO Chemical website <http://www.alcochemical.com/products-markets/combo/water/propAquatreat.asp> printed from the web on Jan. 7, 2005.*

*Primary Examiner*—W. L. Walker
*Assistant Examiner*—Krishnan S. Menon
(74) *Attorney, Agent, or Firm*—DLA Piper Rudnick Gray Cary US LLP

(57) ABSTRACT

A water-treating microbicide, containing an inorganic acid and a corrosion inhibitor, and further containing a carboxylic acid having 8 or less carbon atoms or any of alkali metal salts thereof. The present invention can provide a water-treating microbicide, water treatment method and water treatment apparatus exhibiting a high sterilization effect in a membrane separation device for seawater desalination, etc.

12 Claims, 1 Drawing Sheet

U.S. PATENT DOCUMENTS

| | | |
|---|---|---|
| 5,236,600 A | 8/1993 | Hutchins |
| 5,344,590 A | 9/1994 | Carter et al. |
| 5,776,876 A * | 7/1998 | Garris ................. 510/247 |
| 5,871,691 A * | 2/1999 | Carey et al. ............. 422/17 |
| 5,981,449 A * | 11/1999 | Rapisarda et al. .......... 510/108 |
| 6,468,430 B1 | 10/2002 | Kimura et al. |
| 6,551,553 B1 * | 4/2003 | von Rheinbaben et al. ... 422/28 |
| 2003/0060372 A1 * | 3/2003 | Fan et al. ............... 507/117 |
| 2003/0080058 A1 | 5/2003 | Kimura et al. |

FOREIGN PATENT DOCUMENTS

| | | |
|---|---|---|
| CN | 1240769 A | 1/2000 |
| EP | 0 082 705 A1 | 6/1983 |
| EP | 0 451 434 A1 | 10/1991 |
| EP | 0 807 695 A1 | 11/1997 |
| EP | 1 031 372 A1 | 8/2000 |
| GB | 2 189 394 A | 10/1987 |
| JP | 2000-237546 | 9/2000 |
| JP | 2000-237555 | 9/2000 |
| JP | 2000-301148 | 10/2000 |
| JP | 2002-143849 | 5/2002 |

* cited by examiner

BACTERICIDE FOR USE IN WATER TREATMENT, METHOD FOR WATER TREATMENT AND APPARATUS FOR WATER TREATMENT

TECHNICAL FIELD

The present invention relates to a water-treating microbicide, a water treatment method and a water treatment apparatus.

BACKGROUND ART

Membrane separation techniques are used in wide areas such as desalination of seawater and brackish water, production of medical and industrial pure water and ultrapure water, industrial wastewater treatment and food industry. In such membrane separation, the contamination of the separation device caused by microbes impairs the quality of the obtained permeating water, and furthermore promotes the growth of microbes on the membrane surface and the deposition of microbes and their metabolites on the membrane surface, to lower the permeability and separability of the membrane. To avoid these serious problems, various methods for sterilizing the membrane separation device are proposed, and generally, a microbicide is constantly or intermittently added to the feed liquid. As the microbicide, most generally a chlorine-based microbicide advantageous in view of price and operation is added to achieve a concentration of 0.1 to 50 ppm. Furthermore, an effective sterilization method, in which less expensive sulfuric acid is added to lower the pH of the liquid fed to the membrane separation device to 4 or less, is also developed (EP1031372A). As the piping of the membrane separation device, usually a corrosion resistant metal such as stainless steel is used, but if the addition of sulfuric acid or the like raises the acidity, since the metal goes into the corrosion region of the Pourbaix diagram, the piping is liable to be corroded. In a state where the acidity is low, there are such problems that the sterilization frequency must be increased and that longer sterilization time is necessary for enhancing the sterilization effect.

It would therefore be advantageous to overcome the above-mentioned disadvantages of the prior art by providing a water-treating microbicide and a water treatment method having a high sterilization effect.

SUMMARY OF THE INVENTION

The invention includes the following aspects.

A water-treating microbicide, comprising an inorganic acid, a corrosion inhibitor and a carboxylic acid having 8 or less carbon atoms or alkali metal salts thereof.

A water treatment method, comprising the step of adding an inorganic acid, a corrosion inhibitor and a carboxylic acid having 8 or less carbon atoms or alkali metal salts thereof to a liquid undergoing treatment in any steps before a membrane separation step in a water treatment process using a separation membrane.

A water treatment method, comprising the steps of adding an inorganic acid to a liquid undergoing treatment, to keep the pH at 4 or less intermittently, and adding a corrosion inhibitor to the liquid undergoing treatment, in any steps before a membrane separation step in a water treatment process using a separation membrane.

A water treatment apparatus having a membrane separation device, comprising a means for adding an aqueous solution containing an inorganic acid and a corrosion inhibitor to a liquid undergoing treatment to be fed to the membrane separation device.

A water treatment apparatus having a membrane separation device, comprising a means for feeding an aqueous solution containing an acid and a means for feeding an aqueous solution containing a corrosion inhibitor, respectively, to the liquid fed to the membrane separation device.

Figure 1:
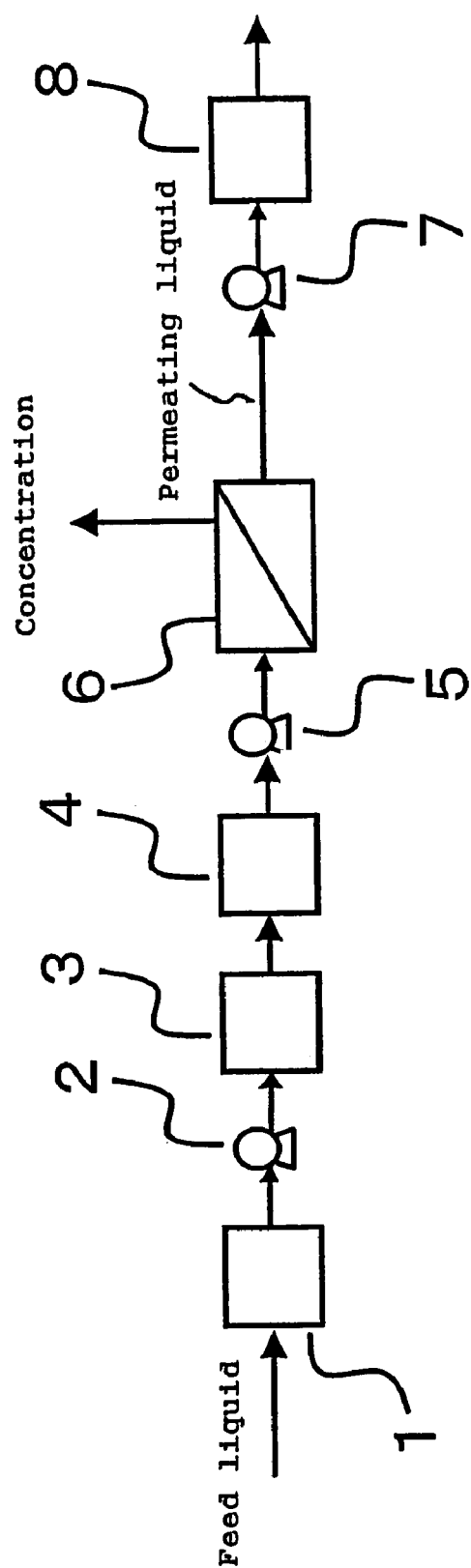
FIG. 1 is a schematic view of water treatment apparatus of this invention.

The Meanings of selected symbols are as follows:
1 water intake device
2 liquid feed pump
3 pre-treatment device
4 intermediate layer and safety filter
5 booster pump
6 membrane separation device
7 liquid feed pump
8 post-treatment device

DETAILED DESCRIPTION

In the present invention, water treatment refers to a process such as the desalting, separation or desalination of seawater or brackish water, production of industrial pure water or ultrapure water, industrial wastewater treatment, separation or concentration in the food industry, or recovery of valuable materials from wastewater.

In this invention, a membrane separation device refers to a device, in which a liquid undergoing treatment is supplied to a membrane module under pressurization for separation into a permeating liquid and a concentrate for the purpose of fresh water generation, concentration or separation, etc. Examples of the membrane module include a reverse osmosis membrane module, ultrafiltration membrane module, microfiltration membrane module, etc. The membrane separation devices can be classified into a reverse osmosis membrane device, ultrafiltration membrane device and microfiltration membrane device, mainly in reference to the membrane module used.

A reverse osmosis membrane device preferably used in this invention is described below as an example. A reverse osmosis membrane device usually consists of a reverse osmosis membrane element, pressure vessel, booster pump, etc. The liquid undergoing treatment to be fed to the reverse osmosis membrane device usually contains chemicals such as a microbicide, coagulant, reducing agent and pH regulator, and it is pretreated by means of coagulation, settling, sand filtration, polishing filtration, active carbon treatment, microfiltration, ultrafiltration, safety filter permeation, etc., before being fed into the device. For example, in the case of seawater desalting, seawater is taken in and separated from particles, etc. in a settling basin, and a microbicide such as chlorine is added to the settling basin for sterilization. In succession, a coagulant such as iron chloride or polyaluminum chloride is added, and sand filtration is carried out. The filtrate is stored in a storage tank and adjusted in pH using sulfuric acid, etc., to be fed. While it is fed, a reducing agent such as sodium hydrogensulfite is added to reduce and remove the microbicide, and the residue is permeated safety filter. Then the filtrate is raised in pressure by a high-pressure pump and fed into a reverse osmosis membrane module.

However, these pre-treatments are selected as required, depending on the liquid to be treated, application, etc.

The reverse osmosis membrane refers to a semi-permeable membrane that allows a component in the liquid such as a solvent to permeate but does not allow the other components to permeate. The materials generally used as the reverse osmosis membrane include high molecular materials such as cellulose acetate polymers, polyamides, polyesters, polyimides and vinyl polymers. As for the structure of the membrane, there are, for example, an asymmetric membrane having a dense layer at least on one side of it and having fine pores gradually increasing in diameter from the dense layer into the membrane or toward the other side, and a composite membrane consisting of the asymmetric film and a very thin active layer made of another material formed on the dense layer. As for the form of the reverse osmosis membrane, there are hollow fiber membranes, flat membrane, etc. Usually it is preferred that the membrane thickness of hollow fiber membranes or flat membrane is 10 µm to 1 mm, and that the outer diameter of the hollow fiber membranes is 50 µm to 4 mm. As a flat membrane, an asymmetric membrane is preferred, and as a composite membrane, it is preferred that a substrate such as a woven fabric, knitted fabric or non-woven fabric, etc. is used as a support. However, the method of the present invention can be used irrespective of the material, structure and form of the reverse osmosis membrane, and is effective in every case.

Typical examples of the reverse osmosis membrane include a cellulose acetate- or polyamide-based asymmetric membrane, and a composite membrane having a polyamide- or polyurea-based active layer. Among them, a cellulose acetate-based asymmetric membrane and a polyamide-based composite membrane are especially effective for the method of this invention, and an aromatic polyamide-based composite membrane is further effective.

A reverse osmosis membrane module is a product formed for actually using the above-mentioned reverse osmosis membrane. In the case where the reverse osmosis membrane is formed as a flat membrane, it can be installed in a spiral, tubular or plate-and-frame module, and in the case of hollow fiber membranes, they are bundled and installed in a module. The present invention can be applied irrespective of these constitutions of reverse osmosis membranes.

The operation pressure of a reverse osmosis membrane device is usually in a range of 0.1 MPa to 15 MPa, and can be selected as required, depending on the liquid to be treated, operation method, etc. In the case where a solution with a low osmotic pressure such as brackish water is going to be treated, the device is operated at a relatively low pressure, and in the case where seawater or industrial wastewater is going to be treated, it is operated at a relatively high pressure.

It is preferred that the operation temperature of the reverse osmosis membrane device is in a range of 0° C. to 100° C. If the temperature is lower than 0° C., the liquid undergoing treatment may be frozen, and if higher than 100° C., the liquid undergoing treatment may evaporate.

The recovery of the liquid undergoing treatment in the reverse osmosis membrane device can be usually selected in a range of 5 to 98%. However, the pre-treatment methods and operation pressure must be taken into account in reference to the properties, concentrations and osmotic pressures of the liquid undergoing treatment and the concentrate, when the recovery is set. For example, in the case of seawater desalination, a recovery of 10 to 40% is usually set, and in the case of highly efficient device, a recovery of 40 to 70% is set. In the case of brackish water desalination or production of ultrapure water, operation can be made usually at a high recovery of 70% or more, as required at 90 to 95%. The recovery refers to a value obtained by dividing the amount of the liquid permeating the reverse osmosis membrane by the amount of the liquid undergoing treatment, and multiplying the quotient by 100.

A reverse osmosis membrane device mainly consists of a high-pressure pump and a reverse osmosis membrane module. As the high-pressure pump, an optimum pump can be selected in response to the operation pressure of the device.

As the reverse osmosis module, one module can be used, but it is preferred to use plural modules disposed in series or parallel to the liquid undergoing treatment. In the case where they are disposed in series, a booster pump can be installed between the reverse osmosis membrane modules. In the case of seawater desalination, in view of equipment cost, especially two modules disposed in series can be preferably used. In this case, it is preferred to install a booster pump between the reverse osmosis membrane modules disposed in series, for raising the pressure of the liquid undergoing treatment to 1.0~5.0 MPa, when feeding it to the latter module. If the reverse osmosis membrane modules are disposed in series to the liquid undergoing treatment, the effect of the present invention is large, since the time during which the liquid undergoing treatment is kept in contact with the membrane modules becomes long.

Furthermore, the reverse osmosis membrane modules can also be disposed in series to the permeating liquid. This is a preferable method in the case where the quality of the permeating liquid is insufficient for use or in the case where it is intended to recover the solute in the permeating liquid. In the case where the reverse osmosis membrane modules are disposed in series to the permeating liquid, it is preferred to install a pump between the reverse osmosis membrane modules, for re-pressurizing the permeating liquid, or for applying a sufficient pressure in the former step for using the remaining pressure in the latter step for membrane separation. Furthermore in the case where the reverse osmosis membrane modules are disposed in series to the permeating liquid, it is preferred to install an acid-adding device between the reverse osmosis membrane modules for sterilizing the latter reverse osmosis membrane module.

In the reverse osmosis membrane device, the portion not permeating the membranes out of the liquid undergoing treatment is taken out as a concentrate from the reverse osmosis membrane modules. The concentrate can be used or thrown away, or can also be further concentrated by any other method. The concentrate can also be partially or wholly circulated into the liquid undergoing treatment. The permeating liquid that has permeated the membranes can be used, thrown away or can also be partially or wholly circulated into the liquid undergoing treatment.

In general, the concentrate of the reverse osmosis membrane device has pressure energy, and for reducing the operation cost, it is preferred to recover the energy. The energy can be recovered by means of an energy recovery device attached to any desired high-pressure pump, but it is preferred to recover the energy by a special turbine type energy recovery pump installed before or after a high-pressure pump or between modules.

It is preferred that the treatment capacity of the membrane separation device used in this invention is 0.5 m$^3$ to 1,000,000 m$^3$ as the amount of water treated per day.

Furthermore, in the membrane separation device used in this invention, it is preferred that the piping in the device has a structure with few retaining portions.

In the water treatment method of this invention, an inorganic acid and a corrosion inhibitor are intermittently added to the liquid undergoing treatment to be fed into the water treatment apparatus. The addition of an inorganic acid is very important in view of giving the sterilization effect, and the effect is remarkable especially in the membrane filtration using seawater as the liquid undergoing treatment. The pH at which microbes are killed is peculiar to each microbe species. For example, in the case of *Escherichia coli*, the lower limit of pH for growth is 4.6, but the bacterium will be killed at pH 3.4 or less. Seawater contains many kinds of microbes, and they are killed respectively at different pH values. However, usually if the liquid undergoing treatment is kept at pH 4.0 or less for a certain period of time, 50 to 100% of microbes can be killed. It is preferred that the pH of the liquid undergoing treatment containing an inorganic acid and a corrosion inhibitor is 3.9 or less. More preferred is 3.7 or less, and especially preferred is 3.4 or less. There is no particular limit for the lower limit of pH, but in view of preventing the corrosion of equipment, 1.5 or more is preferred, and especially 2.0 or more is preferred.

Furthermore, it is preferred that the pH of the liquid undergoing treatment is 3.0 or less, for presenting a high sterilization effect against microbes including aciduric microbes. If the pH is kept constant at 3.0 or less, a high sterilization effect against all the microbes including aciduric microbes can be shown, but the chemical cost for making the feed liquid acidic becomes high while the effect on the corrosion of piping equipment threatens to be large. So, it is preferred in view of efficient sterilization, that during ordinary intermittent sterilization, the pH of the liquid undergoing treatment is kept at as high as higher than 3.0 in a range of 3.0 to 4.0, and that against the microbes still remaining to live without being killed, the liquid undergoing treatment is kept at 3.0 or less at a frequency of once per 2 to 1,000 times of intermittent sterilization.

It is preferred to intermittently add an inorganic acid and a corrosion inhibitor to the liquid undergoing treatment to ensure that the plate count remaining rate in the concentrate is kept at 30% or less after completion of membrane separation, and that the plate count remaining rate is kept at 15% or less at a frequency of once per 2 to 1,000 times of intermittent addition of an inorganic acid. If the plate count remaining rate is more than 30%, sterilization is insufficient. The plate count remaining rate (%) is obtained from the following formula.

Plate count remaining rate (%)={(Plate count after adding the inorganic acid)/(Plate count before adding the inorganic acid)}×100

As the inorganic acid used in this invention, any of hydrochloric acid, sulfuric acid, nitric acid, phosphoric acid, etc. can be used, but in view of economic aspect, the use of sulfuric acid is preferred.

The corrosion inhibitor used in this invention is important for preventing the corrosion of the water treatment apparatus and raising the sterilization effect. As the corrosion inhibitor used in this invention, a compound selected from polycarboxylic acids having at least six carboxylic acid groups in the molecule, ethylenediaminetetraacetic acid, nitrous acid and their alkali metal salts can be preferably used. As the polycarboxylic acid, at least one compound selected from polyepoxysuccinic acids represented by the following general formula (where n is an integer of 3 or more, and X and Y denote, respectively independently, hydrogen or alkali metal), polyacrylic acid, polymaleic acid, and maleic acid copolymers can be preferably used.

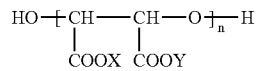

As the corrosion inhibitor, a compound selected from polyepoxysuccinic acids, ethylenediaminetetraacetic acid, polyacrylic acid and their alkali metal salts is especially preferred. Since these compounds have atoms with high electro-negativity such as oxygen and nitrogen in the molecule, they are preferably excellent in adsorbability to the surface of a metal.

Among them, polyacrylic acid is most preferred since it has high food safety and high corrosion-inhibiting effect. Polyacrylic acid is especially preferred in the case where water treatment is intended for production of drinking water.

The optimum range of the weight average molecular weight of polyacrylic acid depends on water treatment conditions such as pH and temperature. So, it is necessary to select polyacrylic acid having a weight average molecular weight suitable for the conditions. It is preferred that the weight average molecular weight of polyacrylic acid is in a range of 500 to 10,000, and a more preferred range is 1,000 to 8,000. If the weight average molecular weight is less than 500, it is difficult to obtain a sufficient corrosion-inhibiting effect, and if more than 10,000, the storage stability of the microbicide is likely to be low.

A polyepoxysuccinic acid or any of alkali metal salts thereof can be synthesized, for example, according to the following method. A maleate is epoxidized using hydrogen peroxide and also using sodium tungstate as a catalyst, to make an epoxysuccinate. Then, the epoxysuccinate is polymerized with ring opening using calcium hydroxide as a catalyst in an alkali aqueous solution, to obtain a polyepoxysuccinate. As the maleic acid copolymer, a copolymer consisting of maleic acid and an olefin, a copolymer consisting of maleic acid and methyl vinyl ether, etc. can be preferably used.

The acid and the corrosion inhibitor can be added separately to the liquid undergoing treatment to be fed to the water treatment apparatus, or a water-treating microbicide containing both mixed beforehand can also prepared and added. The preparation of a water-treating microbicide in advance is preferred, since the sterilization treatment can be carried out efficiently.

It is preferred that the concentrations of the inorganic acid and the corrosion inhibitor in the water-treating microbicide of this invention are in a range of 50 ppm (weight) to 50 wt % respectively. If the concentration of each or either of the acid and the corrosion inhibitor is more than 50%, the storage stability of the microbicide is likely to decline. If the concentration of each or either of the acid and the corrosion inhibitor is less than 50 ppm, it is necessary to increase the added amount of the water-treating microbicide, and the sterilization efficiency is likely to decline.

It is preferred that the water used in the water-treating microbicide of this invention is pure water. If the water used contains impurities, they may react with the acid or corrosion inhibitor, to form a precipitate, and the storage stability may decline.

Since the mixture consisting of an acid and a corrosion inhibitor can happen to be poor in storage stability, it is preferred to further add a storage stabilizer to the water-treating microbicide. As the storage stabilizer, for decreasing the damage to the separation membranes of the water treatment apparatus and for sustaining the sterilization effect, a carboxylic acid having 8 or less carbon atoms or any of alkali metal salts thereof can be preferably used. As the carboxylic acid having 8 or less carbon atoms, preferred is at least one selected from acetic acid, lactic acid, succinic acid, tartaric acid, citric acid and malic acid. If such a storage stabilizer is added, the microbicide containing an acid and a corrosion inhibitor can be stored stably for a long period of time. The optimum range of the concentration of the storage stabilizer in the water-treating microbicide depends on the concentrations of the acid and the corrosion inhibitor in the microbicide, but it is usually preferred that the concentration is in a range of 50 ppm (weight) to 50 wt %.

The water-treating microbicide of this invention can be used in various water treatment processes, but it is preferred to use the microbicide in a water treatment process using a separation membrane greatly affected by microbes.

The separation membranes that can be used in this invention include reverse osmosis membranes, ultrafiltration membranes, microfiltration membranes, etc., but it is preferred that the water-treating microbicide is used in a water treatment process using reverse osmosis membranes for which a generally used oxidizing agent such as chlorine cannot be used.

The acid and the corrosion inhibitor can be added separately to the liquid undergoing treatment to be fed to the water treatment apparatus, or a water-treating microbicide containing both mixed beforehand can also prepared and added. The preparation a water-treating microbicide in advance is preferred, since the sterilization treatment can be carried out efficiently.

It is preferred that the water-treating microbicide is added at a concentration in a range of 10 ppm (weight) to 10 wt % in the liquid undergoing treatment. If the added amount of the microbicide is smaller than 10 ppm, it is necessary to raise the concentrations of the acid and the corrosion inhibitor in the microbicide, for obtaining a high sterilization effect, and in this case, the storage stability of the water-treating microbicide may decline. If the added amount of the water-treating microbicide is larger than 10 wt %, a large load acts on the device used for adding the water-treating microbicide, and the energy consumption becomes large. This may be an economic disadvantage.

It is preferred that the water-treating microbicide is added intermittently. It is preferred that the period of time during which the microbicide is kept added each time is in a range of 0.5 to 2.5 hours, and that the addition frequency is once per day to per month. It is preferred to adequately change the addition period of time and addition frequency, monitoring the variation in the amount of water permeating the membrane, the variations in the plate count and contained organic carbon of the concentrate, the rise of differential pressure, etc. For sterilizing the membranes, the membranes can be immersed in an aqueous solution containing an acid and a corrosion inhibitor while the water treatment apparatus stops operation, but the method of adding the water-treating microbicide to the liquid undergoing treatment during membrane separation is efficient and preferred.

In the water treatment method of this invention, the inorganic acid and the corrosion inhibitor can also be added separately to the liquid undergoing treatment. It is preferred that the amount of the inorganic acid added to the liquid undergoing treatment is 10 ppm (weight) or more in view of sterilization effect, and is 1 wt % or less in view of economy and the corrosion prevention of equipment such as piping.

The preferred amount of the microbicide added to the liquid undergoing treatment depends on the salt concentration of the liquid undergoing treatment, but it is preferred to control to ensure that the pH of the liquid undergoing treatment becomes 4 or less intermittently, and that the concentration of the corrosion inhibitor in the liquid undergoing treatment is kept in a range of 0.1 ppm to 1%. If the pH of the liquid undergoing treatment becomes higher than 4, the sterilization effect can decline. Furthermore, if the concentration of the corrosion inhibitor is lower than 0.1 ppm, the corrosion-inhibiting effect may decline. On the contrary, if the concentration of the corrosion inhibitor is higher than 1%, the corrosion-preventing effect tends to level off, and this may be an economical disadvantage.

If sulfuric acid is used as the inorganic acid, it is preferred to keep the added amount proportional to the salt concentration of the liquid undergoing treatment. For example, when 50 ppm of sulfuric acid was added to a pressure-sterilized (120° C., 15 minutes) physiological salt solution (salt concentration 0.9 wt %), the pH dropped to 3.2, but when seawater samples collected at three places and a commercially available artificial seawater sample (salt concentration about 3.5 wt %) were pressure-sterilized (120° C., 15 minutes) and used as liquids undergoing treatment, the pHs of the liquids undergoing treatment were in a range of 5.0 to 5.8 even if 100 ppm of sulfuric acid was added. This is considered to be mainly the effect due to the M alkalinity of seawater. To keep the pH of seawater at 4 or less, it is usually preferred to add 120 ppm (weight) or more of sulfuric acid. It is preferred that the upper limit in the added amount of sulfuric acid is 400 ppm or less in view of economy and the corrosion prevention of equipment such as piping. More preferred is 300 ppm or less. When the concentrations of sulfuric acid added to the above natural seawater and artificial seawater samples were 150 ppm and 200 ppm, the pH values of the liquids undergoing treatment were respectively 3.2 to 3.6 and 2.8 to 2.9. That is, with the increase in the concentration of sulfuric acid, the pH variation of the liquid undergoing treatment decreases.

The optimum range of the concentration of the corrosion inhibitor in the liquid undergoing treatment depends on the liquid to be treated and water treatment conditions, but a range of 0.1 ppm (weight) to 1 wt % is usually preferred. In view of economy and the convenience of water treatment operation, a range of 1 to 500 ppm is more preferred. For example, in the case where wastewater with a pH of 1.0 and a salt concentration of about 8% is treated at a temperature of 35° C., it is preferred that the concentration of the corrosion inhibitor is in a range of 1 to 100 ppm in the liquid undergoing treatment.

In this invention, the inorganic acid and the corrosion inhibitor can be added at any step before the liquid undergoing treatment is fed to the membrane separation device. For sterilization of the membrane separation device, it is preferred to add them immediately before the membrane separation device. Furthermore, it is preferred to add the inorganic acid on the downstream side of adding the corrosion inhibitor to the liquid undergoing treatment, for inhibiting the corrosion of piping.

It is also a preferred method to add the corrosion inhibitor simultaneously when the inorganic acid is added. In the case where the corrosion inhibitor is expensive, it is preferred, in view of economy, to add it only when the pH of the liquid undergoing treatment is 3.0 or less.

It is preferred to intermittently add the inorganic acid and the corrosion inhibitor. It is preferred that the period of time during which the inorganic acid and the corrosion inhibitor are kept added each time is in a range of 0.5 to 2.5 hours, and that the addition frequency is once per day to per month. It is preferred to adequately change the addition period of time and addition frequency, monitoring the variation in the amount of water permeating the membranes, the variations in the plate count and contained organic carbon of the concentrate, the rise of differential pressure, etc. For sterilizing the membranes, the membranes can be immersed in an aqueous solution containing the acid and the corrosion inhibitor while the water treatment apparatus stops operation.

In the case where the inorganic acid and the corrosion inhibitor are added separately, the addition frequency of the inorganic acid can be different from that of the corrosion inhibitor. For example, the acid can be added for 0.5 to 2.5 hours every other day, and the corrosion inhibitor can be added for the same period of time but at a different frequency, say, once per week. Especially if the corrosion inhibitor is expensive and excellent in the corrosion-inhibiting effect, it is preferred to lower the addition frequency of the corrosion inhibitor in view of economy, for example, to combine the addition of the acid only and the addition of both the acid and the corrosion inhibitor.

The water treatment apparatus having a membrane separation device of the present invention consists of, for example, the following A to H.

A. Water intake device: This device takes in the liquid undergoing treatment as the raw water, and usually consists of an intake pump, chemical injection equipment, etc.
B. Pre-treatment devices communicating to the intake device: These devices pre-treat the liquid undergoing treatment to be fed to the membrane separation device, for removing the suspended matter, emulsified product, etc. in the liquid undergoing treatment, and inject some chemicals.

For example, the devices are disposed in the following order.
B-1 Coagulation filtration device
B-2 Polishing filter An ultrafiltration device and a microfiltration device can also be used instead of B-1 and B-2.
B-3 Chemical injecting equipment for injecting a coagulant, microbicide, pH regulator, etc.
C. Intermediate tank installed as required to communicate to the pre-treatment devices: Having such functions as water quantity control and water quality buffer action.
D. Filter communicating to the intermediate tank, if it is installed, or to the pre-treatment devices, if the intermediate tank is not installed: Having a function of removing solid impurities of the liquid undergoing treatment to be fed to the membrane separation device.
E. Membrane separation device: Consisting of a high-pressure pump and a membrane separation module.

Plural membrane separation devices can also be installed in parallel or in series. If they are installed in series, a pump can be installed between the membrane separation devices for raising the pressure of the liquid undergoing treatment to be fed to the latter membrane separation device.
F. Post-treatment devices communicating to the permeating water outlet of the membrane separation device. For example, the following devices can be exemplified.
F-1 Degasifier: Having a function of removing carbonic acid.
F-2 Calcium column
F-3 Chlorine-injecting device
G. Post-treatment devices communicating to the outlet on the raw water side of the membrane separation device. For example, the following devices can be exemplified.
G-1 Buffer: For example, a neutralizer.
G-2 Discharge equipment
H. Others A wastewater treatment device, etc. can also be installed as required.

The water treatment apparatus of this invention can have a pump installed at a desired place. Furthermore, it is preferred that one or more means for adding the inorganic acid and the corrosion inhibitor or their aqueous solutions are installed in the intake device A or the pre-treatment devices B or before the pre-treatment devices B, or before or after the filter D. Especially it is preferred to install the means before the membrane separation device, i.e., before or after the filter D.

To enhance the effect of this invention, it is preferred that the devices used for adding the water-treating microbicide, inorganic acid and corrosion inhibitor can be automatically controlled, and are respectively provided with a pump capable of adequately controlling the injected amount. Furthermore, it is preferred to install the instruments for measuring the pH values of the liquid undergoing treatment to be fed and the concentrate, the concentration of the corrosion inhibitor, etc. in the apparatus. Moreover, to control the intermittent addition of water-treating microbicide, etc., it is preferred that an instrument capable of measuring time is provided. It is more preferred that an automatic controller allowing the automatic operation of the water treatment apparatus as a whole is provided.

It is preferred that the components of the water treatment apparatus of this invention such as piping and valves are made of materials unlikely to be corroded at pH 4 or less. If the liquid undergoing treatment to be fed is kept at pH 4 or less, a high sterilization effect can be obtained, and the effect of removing the scale in the piping can also be obtained. To prevent the membrane deterioration caused by oxidizing agents of chlorine, etc., sodium hydrogensulfite is added as the case may be, but, since the water-treating microbicide of the present invention is used, the amount of sodium hydrogensulfite can be remarkably decreased.

The addition of a chlorine-based microbicide in a pre-treatment step is effective for sterilization and is generally used. In the case of a treatment apparatus having a membrane separation device, a chlorine-based microbicide is continuously or intermittently injected, for example, in any step of the devices A to D. This method can almost perfectly sterilize the liquid undergoing treatment to be fed unless a resistant strain emerges. A chlorine-based microbicide can chemically deteriorate a reverse osmosis membrane. To prevent deterioration, a reducing agent such as sodium hydrogensulfite is generally added immediately before the membrane separation device. However, in the liquid undergoing treatment remaining after reducing and removing chlorine by a reducing agent, microbes can easily grow. In addition, the microbes are not a variety of microbes existing in the raw seawater before the addition of the microbicide, but a group of as sorted microbes that may include many aciduric microbes. This problem can be solved if the addition of a chlorine-based microbicide in the pre-treatment step and the injection of a reducing agent immediately before the membrane separation device are carried out respectively intermittently. This method is also effective for preventing membrane deterioration. It is preferred that the chlorine-based microbicide is injected once per day to once per six months for about 30 minutes to 2 hours each time, in reference to the quality of raw seawater, i.e., the existence of microbes. In adaptation to the timing of adding the chlorine-based microbicide, and considering the movement of the water containing the chlorine-based microbicide, it is preferred to supply a reducing agent at a position between the pre-treatment devices and the membrane separation device for inactivating the chlorine-based microbicide. In addition, in adaptation to the timing, it is desirable to add the water-treating microbicide of this invention or to add the corrosion inhibitor and the acid separately to the aqueous solution to be fed to the membrane separation device, for sterilizing the membrane separation device.

The intermittent chlorine-based microbicide injection method to the pre-treatment step like this gives an effect of remarkably decreasing the treatment cost such as microbicide cost compared with the continuous injection of microbicide. This can be achieved for the first time with the water treatment method of the present invention using the water-treating microbicide or the acid and the corrosion inhibitor, and could never be achieved by the conventional sterilization methods since the sterilization effect is insufficient.

The water treatment method and apparatus of this invention can be suitably used for the water treatment with a membrane separation device. Particularly it can be suitably used for water refining processes such as desalination of seawater, desalination of brackish water, production of industrial water, production of ultrapure water or pure water, production of medicinal pure water, clarification of raw tap water, and advanced treatment of tap water. Furthermore, it can be used in the concentration of food, or in the case where organic materials, etc. likely to be decomposed by conventional oxidizing microbicides are separated or concentrated, so that they can be concentrated or recovered without being decomposed. Thus, the effect of this invention is large. Moreover, in the case of producing drinking water, this invention has an effect that the generation of the trihalomethane produced with chlorine sterilization can be prevented. Still furthermore, the water treatment method of this invention is especially suitable for the production of drinking water, since compounds with high food safety only can be used for sterilization.

EXAMPLES

This invention is described particularly in reference to examples, but is not limited thereto or thereby.

First of all, the synthesis of the chemical solution used in the examples is described below.

<Example of Synthesizing a Polyepoxysuccinate>

An epoxysuccinate was synthesized as described below according to the method of Payne, et al. (J. Org. Chem., 24, 54 (1959)).

A 2-liter three-neck flask was charged with 280 g of maleic anhydride and 428 ml of ultrapure water for dissolution. To the aqueous solution, 500 g of 48 wt % potassium hydroxide aqueous solution was added dropwise using a dropping funnel with cooling to keep the temperature at room temperature. Then, 18.8 g of sodium tungstate was added, and subsequently 332 g of 35% hydrogen peroxide water was added dropwise. The mixture was stirred for about 30 minutes, and 115 g of 48 wt % potassium hydroxide aqueous solution was gradually added. In this case, the flask was quickly cooled to keep the reaction temperature at 55 to 65° C. Then, the reaction mixture was kept at 65 to 60° C. for 30 minutes, to obtain a potassium epoxysuccinate aqueous solution. The aqueous solution was cooled to room temperature and concentrated to 300 ml, and it was poured into 1 liter of acetone. The produced precipitate was secured by filtration, for isolation as potassium epoxysuccinate.

Then, a 200 ml round bottom flask was charged with 10.4 g of the potassium epoxysuccinate and 50 g of ultrapure water, and 48 wt % potassium hydroxide was added, to adjust the pH of the aqueous solution to 10.3. Furthermore, 0.41 g of calcium hydroxide was added, and reaction was carried out at 80° C. for 6 hours. In succession, the reaction mixture was cooled to room temperature, and the insoluble matter was secured by filtration. A rotary evaporator was used to remove water at a bath temperature of 40° C., to obtain a white solid.

The molecular weight of the obtained polyepoxysuccinate was measured by means of gel permeation chromatography (GPC). Concretely a sample was prepared at a concentration of 200 ppm, and as a standard substance, polyethylene glycol with a known molecular weight was used, to draw a calibration curve, for calculating the molecular weight of the sample. The weight average molecular weight of the obtained polyepoxysuccinate acid was Mw=20900 (n=100, Mw/Mn=1.00).

Examples 1 to 3

Twenty weight percent of sulfuric acid and 0.1 wt % of a corrosion inhibitor shown in Table 1 were added to pure water (electric conductivity 10 μS/cm), to prepare a water-treating microbicide (pH 0.6). Stainless steel test pieces (20 mm×30 mm×1 mm) made of SUS316L and polished with a No. 320 file on the surface were washed with pure water for 60 minutes using an ultrasonic washer, washed with acetone for 60 minutes, and dried in air. The water-treating microbicide was diluted with seawater (electric conductivity 100 mS/cm) to 100 times (microbicide concentration 1 wt %), to make 100 ml of a testing liquid (pH 1.2), and it was placed in each of ten 100 ml polyethylene containers. The stainless steel test pieces were immersed in the containers one by one. The containers were allowed to stand in an 80° C. thermostatic chamber. On the day $4^{th}$ day and $7^{th}$ day after start of immersion, the test pieces were taken out and weighed. The test pieces were washed with pure water for 5 seconds, washed with acetone for 5 seconds, dried in air, and weighed in a silica gel-dried atmosphere using an electronic balance capable of weighing in 0.01 mg. The average value of five test pieces was obtained. The effect of adding the corrosion inhibitor was evaluated as described below.

The weight loss in the period from start of immersion to the $4^{th}$ day (a) and the weight loss in the period from the $4^{th}$ day to $7^{th}$ day (b) were obtained respectively as follows.

Weight loss (a) (g/m$^2$)=(Weight of test piece before immersion−weight of test piece on the $4^{th}$ day)/Surface area of test piece Weight loss (b) (g/m$^2$)=(Weight of test piece on the $4^{th}$ day−Weight of test piece on the $7^{th}$ day)/Surface area of test piece Then, the ratios of the weight losses (a) and (b) caused with the use of corrosion inhibitor to the weight losses (a) and (b) caused without the use of corrosion inhibitor were obtained respectively as described below.

Weight loss (a) ratio=Weight loss (a) caused with use of corrosion inhibitor/Weight loss (a) caused without use of corrosion inhibitor Weight loss (b) ratio=Weight loss (b) caused with use of corrosion inhibitor/Weight loss (b) caused without use of corrosion inhibitor The average value of the weight loss (a) ratio and the weight loss (b) ratio was employed as the weight loss rate. The result is shown in Table 1. (In the table, potassium polyepoxysuccinate is abbreviated as PES, tetrasodium ethylenediaminetetraacetate, as EDTA, and polyacrylic acid, as PA.)

Comparative Example 1

An experiment was carried out as described for Example 1, except that no corrosion inhibitor was added. The result is shown in Table 1. In this comparative example without using any corrosion inhibitor, the weight loss rate was larger than those in Examples 1 to 3, to show that the test pieces were corroded heavily.

TABLE 1

|  | Corrosion inhibitor | Weight loss rate |
| --- | --- | --- |
| Example 1 | PES | 0.37 |
| Example 2 | EDTA | 0.58 |
| Example 3 | PA | 0.67 |
| Comparative Example 1 | Nil | 1.00 |

Examples 4 to 7

Sulfuric acid was added to seawater (electric conductivity 100 mS/cm) for adjusting its pH to 1, and 10 ppm of a corrosion inhibitor shown in Table 2 was added to the seawater, to prepare a testing liquid. Test pieces (20 mm×30 mm×1 mm) made of SUS304 and polished with a No. 320 file on the surface were washed with pure water for 60 minutes using an ultrasonic washer, washed with acetone for 60 minutes, and dried in air. One hundred milliliters of the testing liquid was placed in each of five 100 ml polyethylene containers, and the stainless steel test pieces were immersed in the containers one by one. The polyethylene containers were allowed to stand in a 35° C. thermostatic chamber for 3 days, heated to 80° C. and allowed to stand continuously for 17 hours. The test pieces were taken out, washed with pure water for 30 seconds and washed with acetone for 10 seconds. The weight loss due to corrosion was measured as described below. The weight loss was obtained from the following formula, and the average value of five samples was adopted:

Weight loss $(g/m^2)$=(Weight of test piece before immersion–Weight of test piece after 3 days of immersion)/Surface area of test piece The result is shown in Table 2. (In the table, potassium polyepoxysuccinate is abbreviated as PES, tetrasodium ethylenediaminetetraacetate, as EDTA, and butanetetracarboxylic acid, as BTC.)

Comparative Example 2

An experiment was carried out as described for Example 4, except that no corrosion inhibitor was used.

As can be seen from Table 2, at a strong acid condition of pH 1, in the case where a corrosion inhibitor was added, a high corrosion-inhibiting effect was shown compared with the case where no corrosion inhibitor was added.

TABLE 2

|  | Corrosion inhibitor | Concentration (ppm) | Weight loss $(g/m^2)$ |
| --- | --- | --- | --- |
| Example 4 | PES | 10 | 0.19 |
| Example 5 | EDTA | 10 | 0.14 |
| Example 6 | PA | 10 | 0.38 |

TABLE 2-continued

|  | Corrosion inhibitor | Concentration (ppm) | Weight loss $(g/m^2)$ |
| --- | --- | --- | --- |
| Example 7 | BTC | 10 | 17.9 |
| Comparative Example 2 | Nil | — | 27.9 |

Example 8 and Comparative Examples 3 and 4

Twenty weight percent of sulfuric acid and 0.1 wt % of a corrosion inhibitor shown in Table 3 were added to pure water (electric conductivity 10 μS/cm), to prepare a microbicide for a water treatment apparatus. In Example 8, 0.5 wt % each of sodium citrate and malic acid were further added as storage stabilizers. Stainless steel test pieces (20 mm×30 mm×1 mm) made of SUS304 and polished with a No. 320 file on the surfaces were washed with pure water for 60 minutes using an ultrasonic washer, washed with acetone for 60 minutes, and dried in air. Then, the stainless steel test pieces were immersed in 50° C. 20% nitric acid water for passivation treatment for 1 hour, taken out, washed with acetone and dried in air. The microbicide was diluted with seawater (100 mS/cm) to 100 times (microbicide concentration 1 wt %), to make a testing liquid (pH 1.4), and the testing liquid was placed in five 100 ml polyethylene containers. The stainless steel test pieces were immersed in the containers one by one. The polyethylene containers were allowed to stand in an 80° C. thermostatic chamber. On the 6$^{th}$ day after start of immersion, the test pieces were taken out and weighed. The test pieces were washed with pure water for 5 seconds, washed with acetone for 5 seconds, dried in air, and weighed in a silica gel-dried atmosphere using an electronic balance capable of weighing in 0.01 mg. The weight loss was calculated as described for Example 4. The result is shown in Table 3.

Separately seawater with a salt concentration of 6.9 wt % was allowed to stand at 30° C. overnight to stabilize the plate count, and diluted with sterile water to 3.5 wt % (this is called solution A). To seawater (electric conductivity 100 mS/cm), 0.1 wt % of a microbicide shown in Table 3 was added (pH 3.1) and the solution was allowed to stand at 30° C. for 30 minutes (this is called solution B). For obtaining the plate count, a medium for marine bacteria was used to culture at 30° C. for 6 days, and the number of emerging colonies was counted. The plate count remaining rate to the plate count obtained without pH regulation (solution A) was obtained. That is, the plate count remaining rate was obtained from the following formula.

Plate count remaining rate (%)=[{Plate count after reaction (solution B)}/{Plate count without pH regulation (solution A)}]×100

The result is shown in Table 3.

The microbicide was separately allowed to stand in a 25° C. thermostatic chamber, and the solution state was confirmed on the 19$^{th}$ day. The result is shown in Table 3. (In the table, polyacrylic acid is abbreviated as PA, sodium citrate, as CA, and malic acid, as MA.)

As can be seen from Table 3, compared with Comparative Example 3 in which no storage stabilizer was added, Example 8 in which a storage stabilizer was added showed higher storage stability in addition to the corrosion-inhibiting effect. Comparative Example 4 in which no corrosion inhibitor was added was large in the weight loss of test pieces.

TABLE 3

|  | Corrosion inhibitor | Storage stabilizer | Weight loss (g/m²) | Plate count remaining rate (%) | Solution state |
|---|---|---|---|---|---|
| Example 8 | PA | CA, MA | 0.19 | 0.12 | No Precipitation |
| Comparative Example 3 | PA | Nil | 0.24 | 0.08 | Rather cloudy |
| Comparative Example 4 | Nil | Nil | 1.08 | 0.16 | No precipitation |

INDUSTRIAL APPLICABILITY

The present invention can achieve effective sterilization while inhibiting the corrosion of equipment piping in water treatment using a membrane separation device. Therefore, sterilization frequency can be increased, and pH can be lowered further, to increase the sterilization effect.

Furthermore, in the case where a storage stabilizer is added to the water-treating microbicide of this invention, high storage stability can be realized while the sterilization effect and the corrosion-preventing effect are sustained.

The present invention can be especially suitably used for the processes of seawater desalination, brackish water desalination, etc.

The invention claimed is:

1. A water-treating microbicide, consisting essentially of water, an inorganic acid, a corrosion inhibitor and a carboxylic acid having 8 or less carbon atoms or alkali metal salts of the carboxylic acid, wherein the pH of the microbicide is less than or equal to 4.

2. The water-treating microbicide according to claim 1, wherein the corrosion inhibitor is polyacrylic acid.

3. The water-treating microbicide according to claim 1, wherein the inorganic acid is sulfuric acid.

4. The water-treating microbicide according to claim 1, wherein the concentration of the corrosion inhibitor is in a range of 50 ppm (weight) to 50 wt %.

5. The water-treating microbicide according to claim 2, wherein the molecular weight of the polyacrylic acid is 500 to 10,000.

6. The water-treating microbicide according to claim 1, wherein the carboxylic acid is at least one selected from the group consisting of acetic acid, tartaric acid, succinic acid, citric acid and malic acid.

7. The water-treating microbicide according to claim 1, wherein the corrosion inhibitor is selected from the group consisting of ethylenediaminetetraacetic acid and alkali metal salts thereof, nitrous acid and alkali salts thereof, and polyepoxysuccinic acids represented by general formula (1)

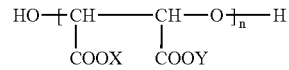

wherein n is an integer of 3 or more, and x and y are, respectively independently hydrogen or alkali metal.

8. The water-treating microbicide according to claim 1, wherein the inorganic acid is present in an amount of 50 ppm–50% by weight, based on the weight of the biocide.

9. The water-treating microbicide according to claim 1, wherein the corrosion inhibitor is present in an amount of 50 ppm–50% by weight, based on the weight of the biocide.

10. The water-treating microbicide according to claim 4, wherein the concentration of the inorganic acid is in a range of 50 ppm (weight) to 50 wt %.

11. A water-treating microbicide consisting essentially of water, an inorganic acid in a concentration in a range of 50 ppm (weight) to 50 wt %, a corrosion inhibitor and a carboxylic acid having 8 or less carbon atoms or alkali metal salts of the carboxylic acid.

12. The water-treating microbicide according to claim 11, wherein the concentration of the corrosion inhibitor is in a range of 50 ppm (weight) to 50 wt %.

* * * * *